United States Patent [19]
Gilbert et al.

[11] Patent Number: 6,121,496
[45] Date of Patent: Sep. 19, 2000

[54] AROMATIC THIOETHER ACYLATION METHOD

[75] Inventors: Laurent Gilbert; Michel Spagnol, both of Lyons, France

[73] Assignee: Rhodia Chemie, Courbevoie, France

[21] Appl. No.: 09/068,625

[22] PCT Filed: Nov. 8, 1996

[86] PCT No.: PCT/FR96/01763

§ 371 Date: Aug. 3, 1998

§ 102(e) Date: Aug. 3, 1998

[87] PCT Pub. No.: WO97/17324

PCT Pub. Date: May 15, 1997

[30] Foreign Application Priority Data

Nov. 10, 1995 [FR] France ................................ 95 13310

[51] Int. Cl.$^7$ ................................................. C07C 319/14
[52] U.S. Cl. ................... 568/42; 568/41; 568/38; 568/56
[58] Field of Search ..................... 568/38, 39, 41, 568/42, 44, 56, 58

[56] References Cited

U.S. PATENT DOCUMENTS 4,593,125   6/1986   Davenport ................................ 568/319
4,638,070   1/1987   Lambelin ................................... 549/23

FOREIGN PATENT DOCUMENTS 334096   3/1989   European Pat. Off. .
459495   5/1991   European Pat. Off. .

OTHER PUBLICATIONS

J Chem Soc Chem Commun by Kawada "Firedel–Crafts Acylation" (14), pp. 1157–1158, 1993.

Stud. Surf. Sci. Catal. (Heterog. Catal. Fine Chem.) vol. 41, 1988, pp. 241–248, XP002004930, B. Coq et al., see pp. 241, 242, 245–248.

Primary Examiner—Gary Geist
Assistant Examiner—Jean F Vollano
Attorney, Agent, or Firm—Jean-Louis Seugnet

[57] ABSTRACT

The present invention relates to a process for the acylation of an aromatic thioether. In its preferred variant, the invention resides in a process for the condensation of acetic anhydride or acetyl chloride with thioanisole. The process for the acylation of an aromatic thioether according to the invention is characterised in that it consists in reacting said thioether with an acylating agent chosen from the group formed by the halides of carboxylic acids and the anhydrides of carboxylic acids, in the presence of an effective quantity of an acid zeolite.

31 Claims, No Drawings

AROMATIC THIOETHER ACYLATION METHOD

This application is an application under 35 U.S.C. Section 371 of International Application Number PCT/FR96/01763, filed on Nov. 8, 1996.

In its preferred variant, the invention resides in a process for the condensation of acetic anhydride or acetyl chloride with thioanisole.

In the following account of the present invention, the term "aromatic thioether" means an aromatic compound of which a hydrogen atom directly linked to the aromatic nucleus is replaced by a thioether group, and the term "aromatic compound" means the conventional notion of aromaticity as defined in the literature, particularly by Jerry MARCH, Advanced Organic Chemistry, 4th edition, John Wiley and Sons, 1992, pp 40 et seq.

A process has been found, and this constitutes the subject matter of the present invention, for the acylation of an aromatic thioether, characterised in that it consists in reacting said thioether with an acylating agent chosen from the group formed by the halides of carboxylic acids and the anhydrides of carboxylic acids, in the presence of an effective quantity of an acid zeolite.

More specifically, the present invention relates to a process for the acylation of an aromatic thioether having the general formula (I):

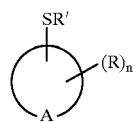

(I)

in which:

A symbolises the radical of a ring forming all or part of an aromatic, monocyclic or polycyclic carbocyclic system, a system containing at least one SR' group: said cyclic radical may bear one or more substituents, R represents one or more substituents which may be the same of different, R' represents an optionally substituted hydrocarbon radical having 1 to 24 carbon atoms, which may be a saturated or unsaturated, linear or branched acyclic aliphatic radical, a saturated, unsaturated or aromatic, monocyclic or polycyclic cycloaliphatic radical, a saturated or unsaturated, linear or branched aliphatic radical bearing a cyclic substituent, R' and R may form a ring optionally containing another heteroatom, n represents the number of substituents on the ring.

In the present disclosure, the term "thioether groups" designates, in a simplified manner, groups of the —S—R' type in which R' has the meaning given above. R' therefore represents both an acyclic or cycloaliphatic, saturated, unsaturated or aromatic aliphatic radical and a saturated or unsaturated aliphatic radical bearing a cyclic substituent.

The aromatic thioether used in the process of the invention corresponds to formula (I) in which R' represents a saturated or unsaturated, linear or branched acyclic aliphatic radical.

More preferably, R' represents a linear or branched alkyl radical having 1 to 12 carbon atoms, preferably 1 to 6 carbon atoms: the hydrocarbon chain may optionally be interrupted by a heteroatom (for example, oxygen), by a functional group (for example —CO—) and/or may bear a substituent (for example, a halogen).

The saturated or unsaturated, linear or branched acyclic aliphatic radical may optionally bear a cyclic substituent. The term ring preferably means a saturated, unsaturated or aromatic carbocyclic ring, preferably cycloaliphatic or aromatic, particularly cycloaliphatic containing 6 carbon atoms in the ring or benzene ring.

The acyclic aliphatic radical may be linked to the ring by a valency bond, a heteroatom or a functional group, and examples are given below.

The ring may optionally be substituted and examples of cyclic substituents may include, inter alia, substituents such as $R_1$ the meaning of which is specified for formula (Ia).

R' may also represent a carbocyclic radical which is saturated or contains 1 or 2 unsaturations in the ring, generally having 3 to 8 carbon atoms, preferably 6 carbon atoms in the ring, said ring may be substituted with substituents such as R.

R' may also represent an aromatic carbocyclic radical, preferably monocyclic, generally having at least 4 carbon atoms, preferably 6 carbon atoms in the ring; said ring may be substituted with substituents such as R.

The process of the invention applies more particularly to aromatic thioethers of formula (I) in which R' represents a linear or branched alkyl radical having 1 to 4 carbon atoms or a phenyl radical.

Examples of radicals R' preferred according to the invention include methyl and ethyl radicals.

In the general formula (I) of aromatic thioethers, the radical A may represent the radical of an aromatic, monocyclic, carbocyclic compound having at least 4 carbon atoms and preferably 6 carbon atoms, or the radical of a polycyclic carbocyclic compound which may be composed of at least 2 aromatic carbocycles and forming, amongst themselves, ortho- or ortho- and pericondensed systems, or of at least 2 carbocycles of which at least one is aromatic and forming amongst themselves ortho- or ortho- and pericondensed systems. More particularly, a naphthalene radical may be mentioned.

The radical A may bear one or more substituents on the aromatic nucleus.

The number of substituents present on the ring depends on the carbon condensation of the ring and on the presence or absence of unsaturations on the ring.

The maximum number of substituents capable of being borne by a ring is easily determined by the man skilled in the art.

In the present disclosure, the term "more" generally means less than 4 substituents on an aromatic nucleus. Examples of substituents are given below but this list is in no way limiting. Any substituent may be present on the ring provided that it does not interfere with the desired product.

The process of the invention applies more particularly to the aromatic thioethers corresponding to formula (Ia):

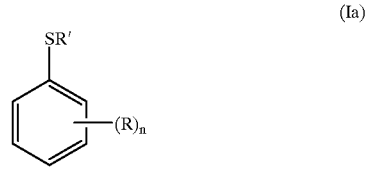

(Ia)

in which:

n is a number lower than or equal to 4, preferably equal to 0, 1 or 2, the radical R' represents a linear or branched alkyl radical having 1 to 6 carbon atoms, preferably 1 to 4 carbon atoms, optionally interrupted by an oxygen atom or a carbonyl group and/or bearing one or more halogen atoms, preferably a chlorine atom, or a phenyl radical, the radical(s) R represent one of the following atoms or groups:
a hydrogen atom,
a linear or branched alkyl radical having 1 to 6 carbon atoms, preferably 1 to 4 carbon atoms such as methyl, ethyl, propyl, isopropyl, butyl, isobutyl, sec.-butyl, tert.-butyl,
a linear or branched alkenyl radical having 2 to 6 carbon atoms, preferably 2 to 4 carbon atoms, such as vinyl, allyl,
a cyclohexyl or benzyl radical,
a linear or branched alkoxy radical having 1 to 6 carbon atoms, preferably 1 to 4 carbon atoms such as methoxy, ethoxy, propoxy, isopropoxy, butoxy, isobutoxy, sec.-butoxy, tert.-butoxy radicals,
an acyl group having 2 to 6 carbon atoms,
a hydroxyl group,
a halogen atom, preferably a fluorine, chlorine or bromine atom,
a trifluoromethyl radical,
an amine group,
two groups R placed on two vicinal carbon atoms may together, and with the carbon atoms which bear them, form a benzene ring,
the radicals SR' and R and the two successive atoms of the benzene ring may form, amongst themselves, a ring having 5 to 7 atoms, optionally containing another heteroatom.

If n is greater than or equal to 1, the radicals R' and R and the 2 successive atoms of the benzene ring may be linked together by an alkylene, alkenylene or alkenylidene radical having 2 to 4 carbon atoms to form a saturated, unsaturated or aromatic heterocycle having 5 to 7 carbon atoms, One or more carbon atoms may be replaced by another heteroatom, preferably sulphur. Thus, the radicals SR' and R may represent a methylenedithio or an ethylenedithio radical.

The process of the invention applies more particularly to the aromatic thioethers corresponding to formula (Ia) in which n is equal to 1, the radical R' represents an alkyl radical having 1 to 4 carbon atoms and R represents a hydrogen atom, an alkyl or alkoxy radical having 1 to 4 carbon atoms or a hydroxyl group.

By way of illustration of compounds corresponding to formula (I), the following may be mentioned more particularly:
thioanisole,
o-thiocresol,
m-thiocresol,
p-thiocresol,
2-thioethyinaphthalene,
S-phenylthioacetate,
3-(methylmercapto)aniline,
S-phenylthiopropionate The compound to which the process of the invention applies more particularly is thioanisole.

It is desirable to use an aromatic thioether having good chemical purity. A purity of at least 97% is desirable.

It may prove necessary to purify the starting substrate, for example, by distillation, in so far as it contains impurities likely to poison the zeolite catalyst.

The acylating reagent is chosen from the group formed by the halides of carboxylic acids and the anhydrides of carboxylic acids.

The said derivatives are derived preferably from saturated or unsaturated, linear or branched aliphatic carboxylic acids or from optionally substituted, saturated or unsaturated cycloaliphatic acids.

More particularly, they correspond to the formula (II):

in which:
$R_1$ represents:
a saturated or unsaturated, linear or branched aliphatic radical having 1 to 24 carbon atoms, a saturated or unsaturated, monocyclic or polycyclic cycloaliphatic radical having 3 to 12 carbon atoms;
X' represents:
a halogen atom, preferably a chlorine or bromine atom,
a —O—CO—$R_2$ radical where $R_2$, which may be the same as or different from $R_1$, has the same meaning as $R_1$; $R_1$ and $R_2$ together may form a saturated or unsaturated, linear or branched aliphatic divalent radical having at least 2 carbon atoms.

The term cyclic substituent refers to the description given above.

More preferably, $R_1$ represents a linear or branched alkyl radical having 1 to 12 carbon atoms, preferably 1 to 6 carbon atoms: the hydrocarbon chain may optionally be interrupted by a heteroatom (for example, oxygen), by a functional group (for example, —CO—), and/or may bear a substituent (for example, a halogen or a $CF_3$ group).

$R_1$ represents preferably an alkyl radical having 1 to 4 carbon atoms, such as methyl, ethyl, propyl, isopropyl, butyl, isobutyl, sec.-butyl, tert.-butyl.

$R_1$ also represents an alkenyl radical having 2 to 10 carbon atoms, such as vinyl, propenyl, butenyl, pentenyl, hexenyl, octenyl, decenyl.

The radical $R_1$ also represents a non-aromatic radical, preferably cycloaliphatic, for example, a cyclohexyl radical, which may optionally be substituted. Any substituent may be present on the ring provided that it does not interfere with the desired product.

More particular examples of substituents include, in particular:
a linear or branched alkyl radical having 1 to 6 carbon atoms, preferably 1 to 4 carbon atoms, such as methyl, ethyl, propyl, isopropyl, butyl, isobutyl, sec.-butyl, tert.-butyl,
a linear or branched alkoxy radical having 1 to 6 carbon atoms, preferably 1 to 4 carbon atoms, such as methoxy, ethoxy, propoxy, isopropoxy, butoxy, isobutoxy, sec.-butoxy, tert.-butoxy radicals,
a halogen atom, preferably a fluorine, chlorine or bromine atom, The preferred acylating agents are acid anhydrides. They correspond more particularly to the formula (II) in which $R_1$ and $R_2$ are the same and represent an alkyl radical having 1 to 4 carbon atoms, optionally bearing halogen atoms, preferably chlorine.

If the acylating agent is an acid halide, it corresponds preferably to formula (II) in which X' represents a chlorine atom and $R_1$ represents an alkyl radical having 1 to 4 carbon atoms, preferably methyl or ethyl optionally bearing halogen atoms, preferably chlorine.

Examples of acylating agents corresponding to formula (II) include, more particularly:

acetic anhydride propanoic anhydride isobutyric anhydride trifluoroacetic anhydride trichloroacetic anhydride monochloroacetyl anhydride monochloroacetyl anhydride acetyl chloride monochloroacetyl chloride dichloroacetyl chloride propanoyl chloride isobutanoyl chloride pivaloyl chloride crotonyl chloride.

In accordance with the process of the invention, the acylation reaction is carried out in the presence of a catalyst composed of an acid zeolite.

The term "zeolite" means a crystalline tectosilicate of natural or synthetic origin, the crystals of which are the result of the three-dimensional assembly of tetrahedral units of $SiO_4$ and $TO_4$; T represents a trivalent element such as aluminium, gallium, boron, iron, preferably aluminium Zeolites of the aluminosilicate type are the most common.

Within the crystalline network, zeolites have a system of cavities linked together by channels with a well defined diameter which are known as pores.

Zeolites may have a unidimensional, two-dimensional or three-dimensional network of channels.

In the process of the invention, a natural or synthetic zeolite may be used.

Examples of natural zeolites which may be used include, for example: chabazite, clinoptilolite, erionite, phillipsite, offretite.

Synthetic zeolites are particularly suitable for the use of the invention.

Examples of synthetic zeolites with a unidimensional network include, amongst others, zeolite ZSM-4, zeolite L, zeolite ZSM-12, zeolite ZSM-22, zeolite ZSM-23, zeolite ZSM-48.

Examples of zeolites with a two-dimensional network used in preference include mordenite, ferrierite.

Zeolites with a three-dimensional network include more particularly zeolite-β, zeolite Y, zeolite X, zeolite ZSM-5, zeolite ZSM-11, offretite.

Synthetic zeolites are used in preference, and more particularly zeolites which take the following forms:

mazzite with an Si/Al molar ratio of 3.4, zeolite L with an Si/Al molar ratio of 1.5 to 3.5, mordenite with an Si/Al molar ratio of 5 to 150, preferably 10 to 100 and even more preferably 10 to 25, ferrierite with an Si/Al molar ratio of 3 to 10, offretite with an Si/Al molar ratio of 4 to 8.5, zeolites β with an Si/Al molar ratio greater than 8, preferably between 10 and 3 5, and even more preferably between 12 and 35, zeolites Y, particularly the zeolites obtained after a dealuminification treatment (for example, hydrotreatment, washing with hydrochloric acid or a treatment with $SiCl_4$) and more particularly zeolites US-Y with an Si/Al molar ratio greater than 3, preferably between 6 and 60, zeolite X of the faujasite type with an Si/Al molar ratio of 0.7 to 1.5, zeolites ZSM-5 or aluminium silicate with an Si/Al molar ratio of 10 to 500, zeolite ZSM-11 with an Si/Al molar ratio of 5 to 30.

Of all these zeolites, zeolites β are used in preference in the process of the invention.

The zeolites used in the process of the invention are known products described in the literature [cf. Atlas of zeolites structure types by W. M. Meier and D. H. Olson published by the Structure Commission of the International Zeolite Association (1992)].

It is possible to use commercially available zeolites or to synthesise them according to processes described in the literature.

Reference may be made to the above-mentioned Atlas, and more particularly, for the preparation:

of zeolite L, to the publication by Barrer R. M. et al., Z. Kristallogr., 128, pp. 352 (1969)

of zeolite ZSM-12, to the US patent 3,832,449 and to the article by LaPierre et al., Zeolites 5, pp. 346 (1985), of zeolite ZSM-22, to the publication by Kokotallo G. T. et at., Zeolites 5, pp. 349 (1985), of zeolite ZSM-23, to the U.S. Pat. No. 4,076,842 and to the article by Rohrman A. C. et al., Zeolites 5, pp. 352 (1985), of zeolite ZSM-48, to the works by Schlenker J. L. et al., Zeolites 5, pp. 355 (1985), of zeolite β, to the U.S. Pat. No. 3,308,069 and to the article by Caullet P. et al., Zeolites 12, pp 240 (1992), of mordenite, to the works by Itabashi et al., Zeolites 6, pp 30 (1986), of zeolites X and Y, to the U.S. Pat. Nos. 2,882,244 and 3,130,007 respectively, of zeolite ZSM-5, to the U.S. Pat. No. 3,702,886 and to the article by Shiralkar V. P. et al., Zeolites 9, pp. 363 (1989), of zeolite ZSM-11, to the works by Harrison I. D. et al., Zeolites 7, pp. 21 (1987).

The zeolite constitutes the catalytic phase. It may be used alone or in mixture with a mineral matrix. In the description, the term "catalyst" will mean the catalyst made wholly of zeolite or in mixture with a matrix prepared according to methods known by the man skilled in the art.

To this end, the matrix may be chosen from metal oxides such as aluminium, silicon and/or zirconium oxides, or from clays and more particularly kaolin, talc or montmorillonite.

In the catalyst, the active phase content represents 5 to 100% of the weight of the catalyst.

The catalysts may take different forms in the process of the invention: powder, formed products such as granules (for example, extrudates or beads), pellets which are obtained by extrusion, moulding, compacting or any other type of known process. In practice, on an industrial scale, granules or beads are the forms having most advantages both in terms of efficiency and in terms of convenience of use.

Whatever the zeolite chosen, a treatment is carried out if necessary which renders it acid.

To this end, conventional treatments are used.

Thus, alkaline cations may be exchanged by submitting the zeolite to a treatment carried out with ammonia thus leading to an exchange of the alkaline cation by an ammonium ion, then calcining the exchanged zeolite in order to decompose the ammonium cation thermally and to replace it by an H⁺ ion.

The amount of ammonia to be used is at least equal to the amount needed to exchange all the alkaline cations for $NH_4^+$ ions.

At least $10^{-5}$ to $5.10^{-3}$ mole of ammonia per gram of zeolite are therefore used.

The exchange reaction of the cation which can be exchanged for $NH_4^+$ is carried out at a temperature between ambient temperature and the reflux temperature of the reaction medium. The operation lasts a few hours and may be repeated.

The zeolite may also be acidified by undergoing a conventional acid treatment. This treatment may be carried out by adding an acid such as, in particular, hydrochloric acid, sulphuric acid, nitric acid, perchloric acid, phosphoric acid and trifluoromethane sulphonic acid.

According to a preferred method of operating, the zeolite is acidified by passage of a volume of acid having a normality between 0.1 and 2 N per gram of zeolite of between 10 ml/g and 100 ml/g. This passage may be carried out in a single stage or preferably in several successive stages.

In accordance with the invention, the acylation reaction is carried out advantageously in the liquid phase containing the aromatic thioether and the acylating agent, in the presence of the catalyst.

One of the starting reagents may act as the reaction solvent but it is also possible to use an organic solvent.

Examples of solvents suitable for the present invention include, in particular, aliphatic or aromatic, halogenated or non-halogenated aliphatic hydrocarbons, aliphatic, cycloaliphatic or aromatic ether oxides.

Examples of aliphatic hydrocarbons include, more particularly, the paraffins such as, in particular, hexane, heptane, octane, nonane, decane, undecane, dodecane, tetradecane or cyclohexane, and naphthalene and aromatic hydrocarbons and more particularly aromatic hydrocarbons such as, in particular, benzene, toluene, xylenes, cumene, petroleum fractions composed of a mixture of alkylbenzenes, particularly fractions of the Solvesso® type.

The aliphatic or aromatic halogenated hydrocarbons include, more particularly, perchlorinated hydrocarbons such as, in particular, tetrachloroethylene, hexachloroethane, partially chlorinated hydrocarbons such as dichloromethane, chloroform, 1,2-dichloroethane, 1,1,1-trichloroethane, 1,1,2,2-tetrachloroethane, pentachloroethane, trichloroethylene, 1-chlorobutane, 1,2-dichlorobutane; monochlorobenzene, 1,2-dichlorobenzene, 1,3-dichlorobenzene, 1,4-dichlorobenzene, 1,2,4-trichlorobenzene or mixture of different chlorobenzenes; bromoform, bromoethane or 1,2-dibromoethane; monobromobenzene or mixtures of monobromobenzene with one or more dibromobenzenes: 1-bromonaphthalene.

Organic solvents that may also be used include aliphatic, cycloaliphatic or aromatic ether oxides and, more particularly, diethyl oxide, dipropyl oxide, dilsopropyl oxide, dibutyl oxide, methyltertiobutylether, dipentyl oxide, diisopentyl oxide, the dimethylether of ethylene glycol (or 1,2-dimethoxyethane), the dimethyl ether of diethylene glycol (or 1,5-dimethoxy 3-oxapentane); benzyl oxide; dioxane, tetrahydrofuran (THF).

Examples of aprotic, more polar organic solvents that may also be used in the process of the invention include, more particularly, nitrated compounds such as, for example, nitromethane, nitroethane, 1-nitropropane, 2-nitropropane or mixtures thereof, nitrobenzene; aliphatic or aromatic nitriles such as acetonitrile, propionitrile, butane nitrile, isobutane nitrile, benzonitrile, benzyl cyanide, linear or cyclic carboxamides such as N,N-dimethylacetamide (DNAC), N,N-diethylacetamide, dimethylformamide (DMF), diethylformamide or 1-methyl-2-pyrrolidinone (NMP); dimethylsulphoxide (DMSO), tetramethylene sulphone (sulpholane); hexamethylphosphotriamide (HMPT).

The preferred solvents are: dichloromethane, tetrachloromethane, THF and diethyl oxide.

It is also possible to use a mixture of organic solvents.

In preference, the starting substrate is used as the reaction solvent.

As mentioned above, the aromatic thioether is allowed to react with an acylating agent, optionally in the presence of a reaction solvent as defined and in the presence of a zeolite catalyst.

The ratio between the number of moles of aromatic thioether and the number of moles of acylating agent may vary because the substrate may act as reaction solvent. Thus, the ratio may be from 0.1 to 10, and is preferably between 0.5 and 4.0.

The amount of catalyst that is used in the process of the invention may vary widely.

If the process is carried out batchwise, the catalyst may represent 0.01 to 50%, preferably 5 to 25% by weight with respect to the aromatic thioether used. However, if the process is carried out continuously, for example by allowing a mixture of aromatic thioether and acylating agent to react on a fixed bed of catalyst, these ratios of catalyst/aromatic thioether have no meaning and at a given moment it is possible to have a weight excess of catalyst with respect to the starting aromatic thioether.

The amount of organic solvent used is generally chosen such that the ratio between the number of moles of organic solvent and the number of moles of aromatic thioether is preferably between 0 and 100, and even more preferably between 0 and 50.

The temperature at which the acylation reaction is brought into effect depends on the reactivity of the starting substrate and that of the acylating agent.

It is between 20° C. and 300° C., preferably between 40° C. and 200° C.

Generally speaking, the reaction is carried out at atmospheric pressure, but lower or higher pressures may also be suitable. Operations are carried out under autogenous pressure if the reaction temperature is higher than the boiling point of the reagents and/or the products.

From a practical point of view, the process may be used batchwise or continuously.

According to the first variant, there are no constraints regarding the use of the reagents. They may be introduced in any order.

After the reagents have been brought into contact, the reaction mixture is brought to the desired temperature.

The other variant of the invention consists in carrying out the reaction continuously in a tubular reactor containing the solid catalyst arranged on a fixed bed.

The aromatic thioether and the acylating agent may be introduced separately or in mixture into the reactor.

They may also be introduced in a solvent of the kind mentioned above.

The residence time of the material flow on the catalyst bed is between 15 mn and 10 hours, for example, and preferably between 30 mn and 5 hours.

At the end of the reaction, a liquid phase is recovered containing the acylated aromatic thioether which may be recovered in a conventional manner, by distillation or recrystallisation in an appropriate solvent, for example water or alcohols (methanol, ethanol) after excess reagents have been removed beforehand.

The process of the invention is particularly suitable for the preparation of 4-(methylthio)acetophenone, by acetylation of thioanisole.

An advantage of the process of the invention is that the acylation reaction is carried out without S-dealkylation of the starting aromatic thioether.

The examples that follow illustrate the invention yet without limiting its scope.

In the examples, the yields mentioned correspond to the following definition:

Yield: $RR_{A.A.} = $ $$\frac{\text{number of moles of acylated aromatic thioether formed}}{\text{number of moles of acylating agent introduced}}\%$$

The examples that follow illustrate the invention yet without limiting its scope.

EXAMPLE 1

In this example, the zeolite used is zeolite β with an Si/Al molar ratio of 12.5 sold by PQ Zeolites under the reference CVB 811BL25.

The following are charged to a closed 30 ml reactor:

5 g (40 mmol) of thioanisole sold by Aldrich (purity= 97%), 2.05 g (20 mmol) of acetic anhydride, 0.5 g of said zeolite β, calcined beforehand at 550° C. under a current of dry air.

The reactor is heated to 90° C. for 8 hours.

After 8 hours, the reaction mixture is filtered, then analysed by gas chromatography.

A reaction yield of 60% is obtained.

EXAMPLE 2

The following are charged to a closed 30 ml reactor:

35 g (282 mmol) of said thioanisole, 28.7 g (282 mmol) of acetic anhydride, 3.5 g of the zeolite β described in Example 1, calcined beforehand at 550° C. under a current of dry air.

The reactor is heated to 90° C. for 8 hours.

After 12 hours, the reaction mixture is filtered, then analysed by gas chromatography.

A reaction yield of 45% is obtained.

EXAMPLE 3

The following example is a comparative example.

The following are charged to a closed 30 ml reactor:

2.5 g of acetic acid, 1 ml of thioanisole in 50 ml of chlorobenzene.

0.5 g of the zeolite β described in Example 1 are then added.

After 10 hours at 200° C., no formation of acetothioanisole is detected.

What is claimed is:

1. A process for the acylation of an aromatic thioether, comprising the step of reacting said thioether with an acylating agent selected from the group consisting of the halides of aliphatic carboxylic acids and the anhydrides of aliphatic carboxylic acids, in the presence of an effective quantity of an acid zeolite, said aromatic thioether having the general formula (I):

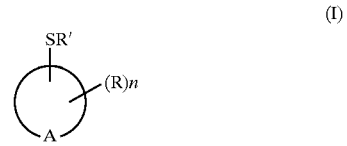

wherein:

A symbolizes the radical of a ring forming all or part of an aromatic, monocyclic or polycyclic carbocyclic system, a system containing at least one SR' group;

the R groups which are the same or different, represent:
a hydrogen atom
a linear or branched alkyl radical having 1 to 6 carbon atoms,
a linear or branched alkenyl radical having 2 to 6 carbon atoms,
a cyclohexyl or benzyl radical,
a linear or branched alkoxy radical having 1 to 6 carbon atoms,
an acyl group having 2 to 6 carbon atoms,
a hydroxyl group,
a halogen atom,
a trifluoromethyl radical, or
an amine group:

R' represents an optionally substituted hydrocarbon radical having 1 to 24 carbon atoms, and n is 0 or a number lower than or equal to 4.

2. A process according to claim 1, wherein R' is a saturated or unsaturated, linear or branched, acyclic aliphatic radical; a saturated, unsaturated or aromatic, monocyclic or polycyclic, cycloaliphatic radical; or a saturated or unsaturated, linear or branched aliphatic radical.

3. A process according to claim 2, wherein R' represents:
a linear or branched alkyl radical having 1 to 12 carbon atoms,
a saturated or unsaturated, linear or branched, acyclic aliphatic radical bearing a substituted cyclic substituent;
a carbocyclic radical which is saturated or contains 1 or 2 unsaturations in the ring, having 3 to 8 carbon atoms in the ring; said ring being optionally substituted, or
an aromatic carbocyclic radical, having at least carbon atoms in the ring; said ring being optionally substituted.

4. A process according to claim 3, wherein R' represents:
a saturated or unsaturated, linear or branched, acyclic aliphatic radical, having 1 to 6 carbon atoms;
a carbocyclic radical which is saturated or contains 1 or 2 unsaturations in the ring, having 6 carbon atoms in the ring; or
a phenyl group.

5. A process according to claim 4, wherein R' represents a linear or branched alkyl radical having 1 to 4 carbon atoms.

6. A process according to claim 5, wherein R' is methyl or phenyl.

7. A process according to claim 1, wherein A represents the radical of a monocyclic, aromatic carbocyclic compound having at least 6 carbon atoms or the radical of a polycyclic carbocyclic compound; the radical A optionally bearing one or more substituents on the aromatic nucleus.

8. A process according to claim 1, wherein A represents the radical of a monocyclic, aromatic carbocyclic compound having 6 carbon atoms.

9. A process according to claim 1, wherein the radicals SR' and R and the two successive atoms of the benzene ring form, amongst themselves, a ring having 5 to 7 atoms.

10. A process according to claim 1, wherein:
n is a number equal to 0, 1, or 2,
the radical R' represents a linear or branched alkyl radical having 1 to 4 carbon atoms, optionally interrupted by an oxygen atom or a carbonyl group or bearing one or more chlorine atom, or a phenyl radical,
the radical(s) R represent:
methyl, ethyl, propyl, isopropyl, butyl, isobutyl, sec.-butyl, tert.-butyl,
vinyl, allyl,
methoxy, ethoxy, propoxy, isopropoxy, butoxy, isobutoxy, sec.-butoxy, tert.-butoxy,
a fluorine, chlorine, or bromine atom.

11. A process according to claim 1, wherein n is equal to 1, the radical R' represents an alkyl radical having 1 to 4 carbon atoms and R represents a hydrogen atom, an alkyl or alkoxy radical having 1 to 4 carbon atoms or a hydroxyl group.

12. A process according to claim 11, wherein the aromatic thioether is thioanisole.

13. A process according to claim 1, wherein the acylating agent corresponds to the formula (II):

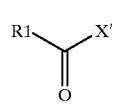

(II)

wherein:
$R_1$ represents:
a saturated or unsaturated, linear or branched aliphatic radical having 1 to 24 carbon atoms; and
X' represents:
a halogen atom or
a radical —O—CO—$R_2$ where $R_2$, which is the same as or different from $R_1$, has the same meaning as $R_1$.

14. A process according to claim 13, wherein the acylating agent corresponds to the formula (II) in which the X' represents a chlorine atom and $R_1$ represents a linear or branched alkyl radical having 1 to 12 carbon atoms; the hydrocarbon chain being optionally interrupted by a heteroatom or by a functional group or bearing substituents; X' represents an —O—CO—$R_2$ radical in which $R_1$ and $R_2$ are the same and represent an alkyl radical having 1 to 4 carbon atoms optionally bearing halogen atoms.

15. A process according to claim 13, wherein the acylating agent is:
acetic anhydride,
propanoic anhydride,
isobutyric anhydride,
trifluoroacetic anhydride,
trichloroacetic anhydride,
monochloroacetyl anhydride,
dichloroacetyl anhydride,
acetyl chloride,
monochloroacetyl chloride,
dichloroacetyl chloride,
propanoyl chloride,
isobutanoyl chloride,
pivaloyl chloride, or
crotonyl chloride.

16. A process according to claim 1, wherein the zeolite is chabazite, clinoptilolite, erionite, mordenite, phillipsite, or offretite.

17. A process according to claim 1, wherein the zeolite is a synthetic zeolite with a unidimensional network.

18. A process according to claim 17, wherein the zeolite is zeolite ZSM-4, zeolite L, zeolite ZSM-12, zeolite ZSM-22, zeolite ZSM-23, or zeolite ZSM-48.

19. A process according to claim 1, wherein the zeolite is a synthetic zeolite with a two-dimensional network.

20. A process according to claim 19, wherein the zeolite is mordenite, or ferrierite.

21. A process according to claim 1, wherein the zeolite is a synthetic zeolite with a three-dimensional network.

22. A process according to claim 21, wherein the zeolite is zeolite-β, zeolite Y, zeolite X, zeolite ZSM-5, zeolite ZSM-11, or offretite.

23. A process according to claim 1, wherein the zeolite is a zeolite β with an Si/Al molar ratio greater than 8, or a zeolite US-Y with an Si/Al molar ratio greater than 3.

24. A process according to claim 23, wherein the Si/Al molar ratio of the zeolite β is between 12 and 35, and the Si/Al molar ratio of the, zeolite US-Y is between 6 and 60.

25. A process according to claim 1, wherein the acylation is carried out in an aqueous medium or in the presence of an optionally halogenated organic solvent.

26. A process according to claim 25, wherein the solvent is an aliphatic or aromatic hydrocarbon, an aliphatic, cycloaliphatic or aromatic ether oxide, an aprotic polar solvent, a nitrated compound, an aliphatic or aromatic nitrile, a linear or cyclic carboxamide, dimethylsulphoxide, tetramethylenesulphone, or hexamethylphosphotriamide.

27. A process according to claim 1, wherein the ratio between the number of moles of aromatic thioether and the number of moles of acylating agent is between 0.1 and 10.

28. A process according to claim 1, wherein the amount of zeolite represents 0.01 to 50% by weight with respect to the aromatic thioether used.

29. A process according to claim 1, wherein the acylation is carried out at a temperature of between 20° C. and 300° C.

30. A process according to claim 1, wherein the acylation is carried out batchwise or continuously.

31. A process according to claim 13, wherein X' is chlorine or bromine.

* * * * *